United States Patent
Akita et al.

(10) Patent No.: US 8,518,247 B2
(45) Date of Patent: Aug. 27, 2013

(54) ERROR CORRECTION FOR A LIQUID CONCENTRATION DETECTOR OF A BLOOD PURIFICATION APPARATUS

(75) Inventors: Kunihiko Akita, Shizuoka (JP); Tomoya Murakami, Shizuoka (JP); Takayuki Hirano, Shizuoka (JP); Yasushi Takakuwa, Shizuoka (JP)

(73) Assignee: Nikkiso Co., Ltd., Tokyo (JP)

( * ) Notice: Subject to any disclaimer, the term of this patent is extended or adjusted under 35 U.S.C. 154(b) by 324 days.

(21) Appl. No.: 12/967,562

(22) Filed: Dec. 14, 2010

(65) Prior Publication Data

US 2011/0139690 A1   Jun. 16, 2011

(30) Foreign Application Priority Data

Dec. 14, 2009   (JP) ................................ 2009-282877

(51) Int. Cl.
*B01D 61/30*   (2006.01)
(52) U.S. Cl.
USPC ......... 210/94; 210/96.2; 210/321.6; 210/646; 356/39; 356/448
(58) Field of Classification Search
USPC ............. 210/94, 96.1, 96.2, 739, 321.6, 645, 210/745; 356/39, 448; 422/82.05
See application file for complete search history.

(56) References Cited

U.S. PATENT DOCUMENTS

| | | | | |
|---|---|---|---|---|
| 3,441,136 A | * | 4/1969 | Wilson, Jr. et al. | 210/90 |
| 4,017,190 A | * | 4/1977 | Fischel | 356/40 |
| 4,180,610 A | * | 12/1979 | Verma | 428/216 |
| 5,670,050 A | * | 9/1997 | Brose et al. | 210/646 |
| 6,284,142 B1 | * | 9/2001 | Muller | 210/745 |
| 6,666,840 B1 | | 12/2003 | Falkvall et al. | |
| 6,947,131 B2 | * | 9/2005 | O'Mahony et al. | 356/218 |
| 7,422,693 B2 | * | 9/2008 | Carter et al. | 210/745 |
| 2005/0051466 A1 | * | 3/2005 | Carter et al. | 210/94 |

\* cited by examiner

*Primary Examiner* — Joseph Drodge
(74) *Attorney, Agent, or Firm* — McDermott Will & Emery LLP

(57) ABSTRACT

A blood purification instrument for extracorporeally circulating a patient's blood and a concentration detector detects a concentration of liquid during blood purification wherein the concentration detector has a light emitter irradiating light onto the liquid, a light receiver receives the light as transmitted through the liquid, a reference light receiver receives reference light branched from the light emitter without transmission through the liquid, and a detector detecting the light intensity respectively of the transmitted light and the reference light received by the light receiver and the reference light receiver, respectively. The blood purification apparatus further includes an error corrector detecting the concentration of the liquid based on the received light intensity of the light received by the light receiver and detected by the detector and for correcting a detected error of the concentration detector based on the received light intensity of the reference light received by the reference light receiver.

9 Claims, 3 Drawing Sheets

US 8,518,247 B2

ERROR CORRECTION FOR A LIQUID CONCENTRATION DETECTOR OF A BLOOD PURIFICATION APPARATUS

CROSS REFERENCE TO RELATED APPLICATIONS

The present application claims priority under 35 U.S.C. §119 to Japanese Patent Application No. 2009-282877, filed Dec. 14, 2009, which is incorporated herein by reference.

FIELD OF THE INVENTION

The present invention relates to a blood purification apparatus having a blood purification instrument for extracorporeally circulating blood of a patient and a concentration detector detecting a concentration of liquid flowing during blood purification.

BACKGROUND OF THE INVENTION

Hemodialysis treatment is a blood treatment purifying extracorporeally circulating blood of a patient. In hemodialysis treatment, a dialyzer is used as a blood purification instrument for flowing therethrough a dialysate, and a blood circuit for extracorporeally circulating blood of a patient is connected to the dialyzer through which the blood and the dialysate contact each other via dialysis membranes within the dialyzer so as to remove waste materials and excess water in blood (the removal of excess water is usually called as "ultrafiltration"). The blood purified by the dialyzer is returned into a body of a patient and, on the other hand, the blood waste material and excess water are discharged outside, together with the dialysate, via a dialysate discharging line.

The waste materials removed from blood contain urea, uric acid, creatinine etc. and variations of the concentration of urea in blood is an effective indicator of dialysis efficiency. Accordingly, it has been proposed to monitor the variation in urea concentration to obtain proper dialysis efficiency. Although it is usually possible to know the variation in the urea concentration via a regularly performed blood examination, it is impossible to monitor the variation in urea concentration in real time during a dialysis treatment.

Accordingly, it has been proposed to arrange a discharged liquid concentration sensor on a dialysate discharging line so as to detect the variation in urea concentration (i.e. an indication such as "Kt/V") in real time (see e.g. JP 2002-516722 below). Such a conventional discharged liquid concentration sensor usually comprises LED(s) (light emitting means) for irradiating light on to discharged liquid from a dialyzer, a light receiving element(s) (light receiving means) for receiving light from the LED(s) transmitted through the discharged liquid, and a detecting means for detecting a received light intensity received by the light receiving element(s) and is structured so that the concentration of discharged liquid can be detected based on the received light intensity detected by the detecting means.

However, in the blood purification apparatus of the prior art, there is concern that the discharged liquid concentration sensor is liable to be influenced by heat within a dialysis apparatus body and thus an error in the detection of concentration may be increased since the discharged liquid concentration sensor is arranged on a dialysate discharging line within the dialysis apparatus body. In particular, since liquids (dialysate and cleaning liquid) are warmed or heated (the cleaning liquid is boiled water), large temperature variation within the dialysis apparatus body is caused. Thus, values of resistors of a light emitting means e.g. of a discharged liquid concentration sensor would be varied and accordingly the emitting light intensity would be greatly varied.

It is, therefore, an object of the present invention to provide a blood purification apparatus that can minimize the detection error of liquid concentration caused by temperature variation and thus improves the accuracy of detection of liquid with a concentration detecting means.

SUMMARY OF THE INVENTION

According to the present invention, there is provided a blood purification apparatus including a blood purification instrument for extracorporeally circulating blood of a patient and a concentration detecting means for detecting a concentration of liquid flowing during blood purification characterized in that the concentration detecting means comprises a light emitting means for irradiating light onto said liquid, a light receiving means for receiving light from the light emitting means transmitted through said liquid, a reference light receiving means for receiving reference light branched from the light emitting means without being transmitted through said liquid, and a detecting means for detecting the light intensity respectively of the transmitted light received by the light receiving means and the reference light received by the reference light receiving means, and that the blood purification apparatus further comprises an error corrector detecting the concentration of the liquid based on the received light intensity of the transmitted light received by the light receiving means and detected by the detecting means and for correcting a detected error of the concentration detecting means based on the received light intensity of the reference light received by the reference light receiving means.

It is preferable that the error corrector comprises a correcting device correcting a current supplied to the light emitting means so that a light amount irradiated by the light emitting means is constant with passage of time based on the intensity of the reference light received by the reference light receiving means.

In another example, the error corrector includes a correcting device correcting a detected value detected by the detecting means based on the intensity of the reference light received by the reference light receiving means.

Further, the light emitting means can include LED(s) and both the light receiving means and the reference light receiving means comprise a light receiving element(s) generating a voltage corresponding to the received light intensity.

Also, the concentration detecting means is a discharged liquid concentration sensor which can monitor the blood purification efficiency by detecting the concentration of the discharged liquid discharged from the blood purification instrument.

Additionally, the concentration detecting means is a blood leakage detector that can detect blood leakage from the concentration of discharged liquid from the blood purification instrument.

Another example is that the concentration detecting means is arranged on a blood circuit, which circulates blood of a patient extracorporeally, and comprises a blood concentration sensor that can detect the concentration of blood flowing through the blood circuit.

According to an example, since the blood purification apparatus further has an error corrector detecting the concentration of the liquid based on the received light intensity of the transmitted light received by the light receiving means and detected by the detecting means and for absorbing a detected error of the concentration detecting means based on the light intensity of the reference light received by the reference light receiving means, it is possible to minimize the detecting error of liquid concentration caused by temperature variation and thus to improve the accuracy of detection of liquid with a concentration detecting means.

According to another example, since the error corrector includes a correcting device correcting a current supplied to the light emitting means based on the intensity of the reference light received by the reference light receiving means so that a light amount irradiated by the light emitting means is constant with the passage of time, it is possible to automatically carry out the correction for error absorption in the concentration detecting means.

According to the present invention, since the error corrector has a correcting device correcting a detected value detected by the detecting means based on the intensity of the reference light received by the reference light receiving means, the correction of supplying current to the light emitting means may not be necessary and thus it is possible to carry out the correction for error absorption in the concentration detecting means reliably and smoothly.

According to another example of the present invention, since the light emitting means comprises LED(s) and both the light receiving means and the reference light receiving means comprise a light receiving element(s) generating a voltage corresponding to the received light intensity, it is possible to provide the concentration detecting means with technical merits of LED.

According to a further example, since the concentration detecting means is a discharged liquid concentration sensor which can monitor the blood purification efficiency by detecting the concentration of the discharged liquid discharged from the blood purification instrument, it is possible to improve the accuracy of detection of the concentration of discharged liquid during blood purification treatment and to monitor the efficiency of blood purification in real time with high accuracy.

Since the concentration detecting means can be a blood leakage detector, which can detect blood leakage from the concentration of discharged liquid from the blood purification instrument, it is possible to improve the accuracy of blood leakage detection in discharged liquid during blood purification treatment.

Accordingly, since the concentration detecting means is arranged on a blood circuit and comprises a blood concentration sensor that can detect the concentration of blood flowing through the blood circuit, it is possible to improve the accuracy in detection of blood concentration during the blood purification treatment.

DETAILED DESCRIPTION OF THE INVENTION

Examples of the present invention are described hereafter with reference to the drawings.

Figure 1:
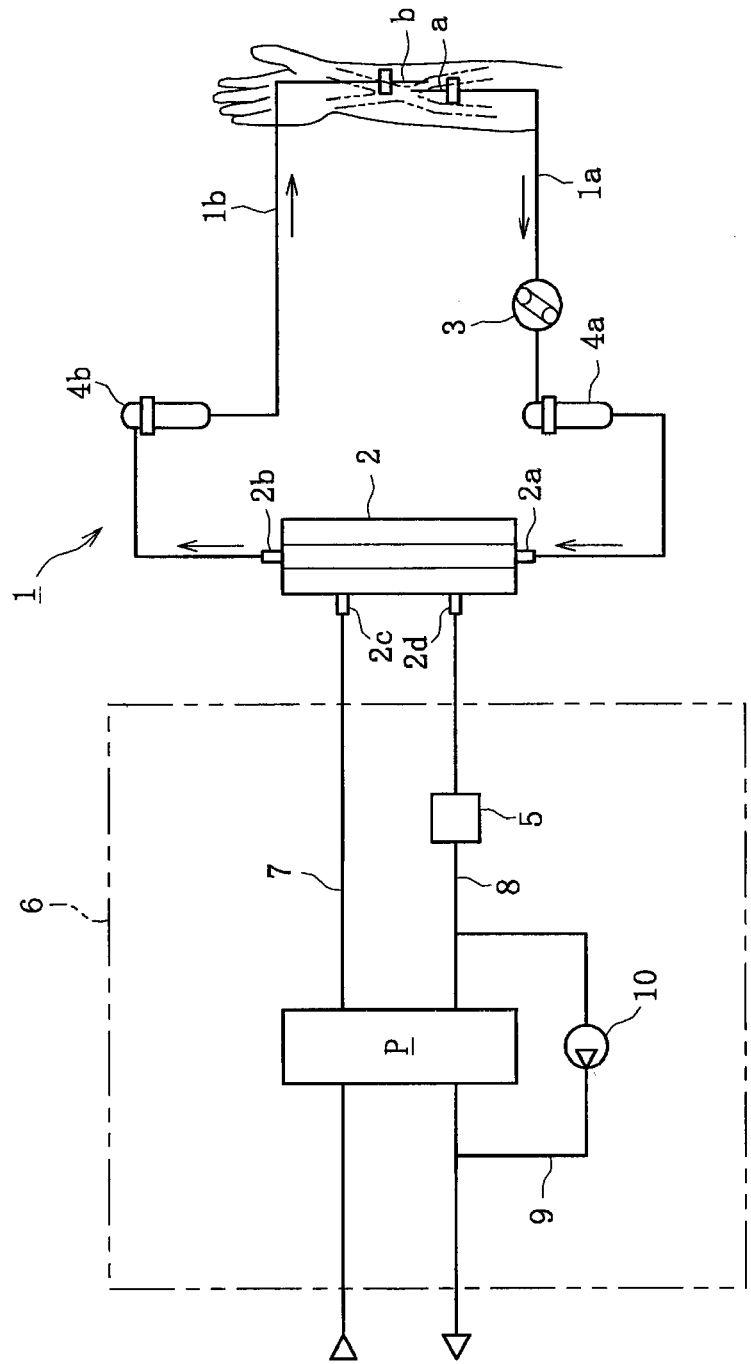
FIG. 1: A schematic view showing an example of the blood purification apparatus of the present invention.

A blood purification apparatus of the present invention is used for purifying blood of a patient with its extracorporeal circulation and can be applied to a hemodialysis apparatus used in hemodialysis treatment. As shown in FIG. 1, such a hemodialysis apparatus generally comprises a dialyzer 2 as a blood purification instrument, a blood circuit 1 connected to the dialyzer 2, a discharged liquid concentration sensor 5 as a concentration detecting means, and dialysis apparatus body 6 for performing ultrafiltration and supplying dialysate to the dialyzer 2.

The blood circuit 1 mainly includes, as shown in FIG. 1, an arterial blood circuit 1a and a venous blood circuit 1b respectively formed of a flexible tube and the dialyzer 2 is arranged between these blood circuits 1a, 1b and connected to them. An arterial puncture needle "a" is adapted to be connected to a tip of the arterial blood circuit 1a, and a peristaltic blood pump 3 and a drip chamber 4a for bubble removal are arranged on the arterial blood circuit 1a. On the other hand, a venous puncture needle "b" is adapted to be connected to a tip of the venous blood circuit 1b, and a drip chamber 4b for bubble removal is arranged on the venous blood circuit 1b.

The arterial puncture needle "a" and the venous puncture needle "b" are inserted respectively into an artery and a vein of a patient. After the blood pump 3 is started and the blood of the patient then flows through the arterial blood circuit 1a to the dialyzer 2 via the drip chamber 4a for bubble removal. The blood of a patient is purified and ultrafiltrated by the dialyzer 2 and finally returned to the vein of a patient through the venous blood circuit 2 after having air bubbles removed by the drip chamber 4b. That is, the blood of a patient can be purified by the dialyzer 2 via the extracorporeal circulation through the blood circuit 1.

A casing of the dialyzer 2 is provided with a blood inlet port 2a, a blood outlet port 2b, a dialysate inlet port 2c and a dialysate outlet port 2d. In the casing, a base end of the arterial blood circuit 1a is connected to the blood inlet port 2a and a base end of the venous blood circuit 1b is connected to the blood outlet port 2b. In addition, a dialysate introducing line 7 and a dialysate discharging line 8 are connected respectively to the dialysate inlet port 2c and the dialysate outlet port 2d.

A large number of hollow fibers (not shown) are contained within the dialyzer 2 and a hollow space of each fiber forms a flowing passage of blood and a space formed between an outer circumferential surface of each fiber and an inner circumferential surface of the casing of the dialyzer 2 forms a flowing passage of dialysate. A wall of each hollow fiber is formed with a vast number of micro apertures (pores) passing through the wall between its inner and outer circumferential surfaces and thus the wall forms a membrane of the hollow fiber. Thus, the waste materials and excess water etc. in blood can pass through the membrane of the hollow fiber into the dialysate flowing around each hollow fiber.

On the other hand, the dialysis apparatus body 6 comprises mainly a duplex pump P, a bypass line 9 connected to the dialysate discharging line 8 bypassing the duplex pump P, and an ultrafiltration pump 10 arranged on the bypass line 9. The duplex pump P is arranged as bridging the dialysate introducing line 7 and the dialysate discharging line 8 and used for supplying the dialysate to the dialyzer 2 through the dialysate introducing line 7 and discharging the dialysate from the dialyzer 2 together with waste material in blood through the dialysate discharging line 8.

One end of the dialysate introducing line 7 is connected to the dialysate inlet port 2c of the dialyzer 2 and the other end of the dialysate introducing line 7 is connected to a dialysate supplying apparatus (not shown), which is for preparing dialysate of predetermined concentration. In addition, one end of the dialysate discharging line 8 is connected to the dialysate outlet port 2d of the dialyzer 2 and the other end of the dialysate discharging line 8 is connected to a solution discharging means (not shown). Accordingly, the dialysate supplied from the dialysate supplying apparatus to the dialyzer 2 through the dialysate introducing line 7 is adapted to be returned from the dialyzer 2 to the solution discharging means through the dialysate discharging line 8 and the bypass line 9.

The ultrafiltration pump 10 is used for removing water from blood of a patient flowing in the dialyzer 2. In particular, when the ultrafiltration pump 10 is driven, an amount of a liquid discharged from the dialysate discharging line 8 becomes more than an amount of the dialysate introduced to the dialyzer 2 through the dialysate introducing line 7 and the increased amount of the liquid corresponds to an amount of water removed from blood. It may be possible to remove water from blood of a patient by using means (e.g. a so-called "balancing chamber" etc.) other than the ultrafiltration pump 10.

Figure 3:
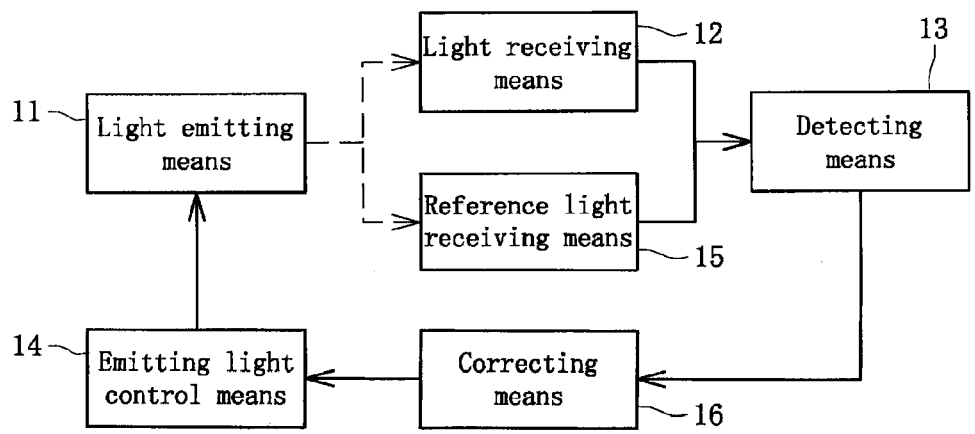
FIG. 3: A block diagram showing the concentration detecting means of FIG. 2.

The discharged liquid concentration sensor 5 (concentration detecting means) is arranged on the dialysate discharging line 8 within the dialysis apparatus body 6 to monitor the efficiency of blood purification by detecting concentration of a liquid (liquid discharged from the dialyzer 2 as a blood purification instrument in the present invention) flowing during the blood purification treatment. The discharged liquid concentration sensor 5 mainly comprises, as shown in FIG. 3, a light emitting means 11, a light receiving means 12, a detecting means 13, an emitting light control means 14, a reference light receiving means 15, and a correcting device 16 as an error corrector.

Figure 2:
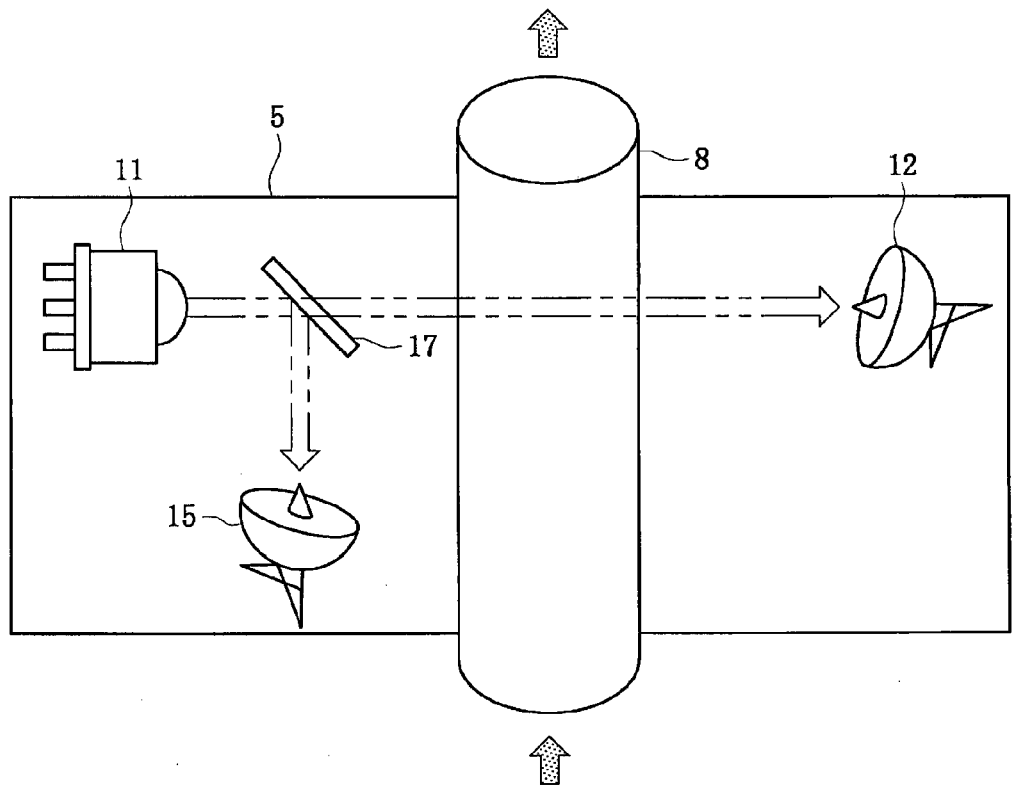
FIG. 2: An enlarged schematic view showing a concentration detecting means of the blood purification apparatus of FIG. 1.

The light emitting means 11 is a light source comprising LED(s) irradiating light onto the liquid (liquid discharged from the dialyzer 2 in the present invention) and arranged opposite to the light receiving means 12 via the dialysate discharging line 8 as shown in FIG. 2. The light receiving means 12 is intended to receive light from the light emitting means 11 transmitted through the liquid (liquid discharged from the dialyzer 2) and comprises, in the present invention, light receiving element(s) generating a voltage corresponding to a received light intensity.

When light from the light emitting means 11 is irradiated onto the dialysate discharging line 8 through which discharged liquid flows, the irradiated light is transmitted through the discharged liquid, there being absorbed by an amount corresponding to the concentration of the discharged liquid, and received by the light receiving means 12. Thus, it is possible to detect the variation of concentration of the discharged liquid by detecting the received light intensity (i.e. a voltage generated in accordance with the received light intensity) using the light receiving means 12.

The detecting means 13 is electrically connected to both the light receiving means 12 and the reference light receiving means 15 to detect the received light intensity (voltage in accordance with the received light intensity in the present invention) of them. The emitting light control means 14 is intended to control an amount of emitting light by the light emitting means 11 and comprises e.g. a digital amplifier, which can control a current supplied to the light emitting means 11.

A half mirror 17 is arranged on an optical path between the light emitting means 11 and the light receiving means 12 as well as on the opposite side of the dialysate discharging line 8 from the light receiving means 12 and the reference light receiving means 15 is arranged on an optical path branched from the light emitting means 11 at the half mirror 17. The reference light receiving means 15 comprises a light receiving element(s) generating a voltage corresponding to the received light intensity similar to the light receiving means 12 and can receive reference light (basic light) branched from the light emitting means 11 without being transmitted through the discharged liquid.

The correcting device (error corrector) 16 is intended to minimize the detecting error of liquid concentration by correcting for thermal drift that causes an error in the discharged liquid concentration sensor 5 based on the received light intensity of the reference light detected by the reference light receiving means 15. In the present invention, the correcting means 16 is electrically connected to both the detecting means 13 and the emitting light control means 14 and adapted to make the emitting light control means 14 to correct the supplying current to the light emitting means 11 based on the received light intensity of the reference light detected by the reference light receiving means 15 so that the amount of irradiated light from the light emitting means 11 is constant with passage of time.

The structure of the present invention as described above makes it possible to detect the concentration of discharged liquid flowing through the dialysate discharging line 8 based on the received light intensity (i.e. voltage caused in accordance with the received light intensity detected by the light receiving means 12) detected by the detecting means 13. In addition, since the supplying current to the light emitting means 11 can be corrected so that the amount of irradiated light from the light emitting means 11 is constant with passage of time based on the received light intensity of the reference light detected by the reference light receiving means 15, it is possible to maintain accuracy of the discharged liquid concentration sensor 5, which is calibrated prior to dialysis treatment, by preventing detection error due to temperature variation.

Figure 4:
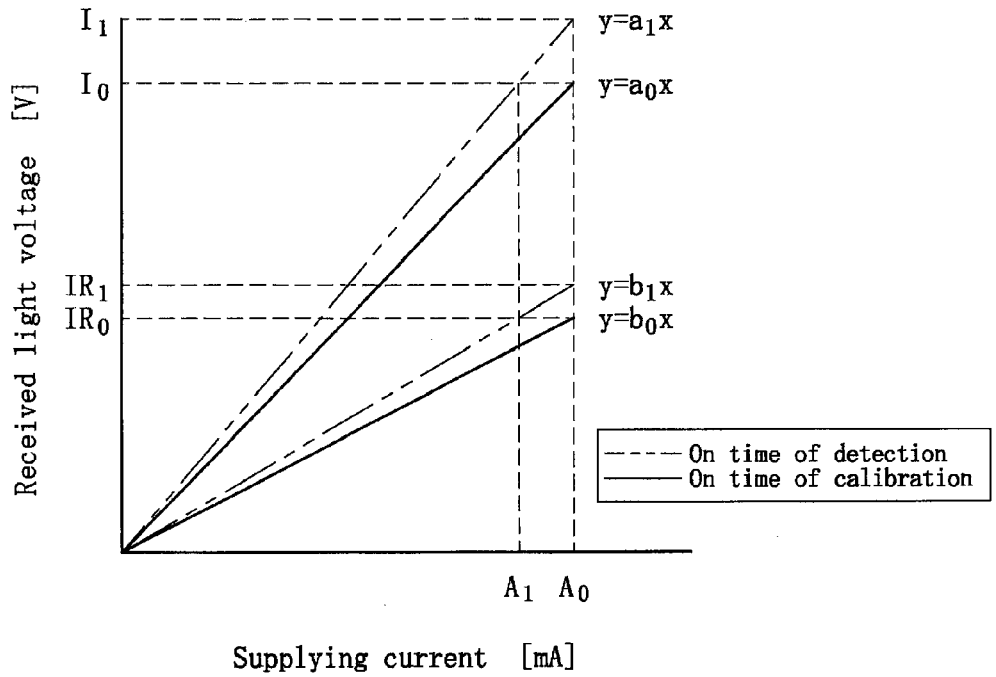
FIG. 4: A graph for explaining a correcting method according to a correcting means of the concentration detecting means.

Next, a method of correction carried out by the correcting means 16 in the discharged liquid concentration sensor (concentration detecting means) 5 is described with reference to a graph of FIG. 4.

It is possible to carry out detection of concentration of discharged liquid at a time of the blood purification treatment (i.e. under a condition in which blood is extracorporeally circulated through the blood circuit 1) after a predetermined calibration but before the blood purification treatment (before dialysis treatment as well as before extracorporeal circulation of blood through the blood circuit 1).

Here, a relation between the supplying current to the light emitting means 11 on a time of calibration and the received light voltage of the light receiving means 12 is expressed as a linear function "$y=a_0 \cdot x$", and a relation between the supplying current to the light emitting means 11 at a time of detection of concentration (at a time of commencement of measurement of concentration of the discharged liquid) and the received light voltage of the light receiving means 12 is expressed as a linear function "$y=a_1 \cdot x$". Additionally, it is assumed that the received light voltage of the light receiving means 12 has varied from "$I_0$" to "$I_1$" due to the thermal drift caused by temperature variation. Here, the supplying current for correcting the thermal drift is defined as "$A_1$" by setting a supplying current as "$A_1$" when the received light voltage is "$I_0$" and a supplying current as "$A_0$" when the received light voltage is "$I_1$".

On the other hand, a relation between the supplying current to the light emitting means 11 at a time of calibration and the received light voltage of the reference light receiving means 15 is expressed as a linear function "$y=b_0 \cdot x$", and a relation between the supplying current to the light emitting means 11 at a time of detection of concentration (at a time of commencement of measure of concentration of the discharged liquid) and the received light voltage of the reference light receiving means 15 is expressed as a linear function "$y=b_1 \cdot x$". In addition, it is defined that the received light voltage is $IR_1$ when supplying current is $A_0$ at a time of detection, and the received light voltage is $IR_0$ when the supplying current is $A_1$.

Thus, since the relation between the received light voltage $IR_0$ and supplying current $A_0$ is "$IR_1=b_1 \cdot A_0$", a mathematical formula (1) such as "$b_1=IR_1/A_0$" can be obtained. Furthermore, it is possible to obtain the supplying current $A_1$ for correcting a cause of error (thermal drift) due to the temperature variation from a mathematical formula (2) such as "$IR_0=b_1 \cdot A_1$" and the mathematical formula (1). That is, it is possible to obtain the supplying current $A_1$ for correcting the thermal drift to be controlled by the emitting light control means 14 by substituting parameters in an operational expression such as "$A_1=IR_0/b_1=IR_0/IR_1 \times A_0$".

The correction described above is performed at a predetermined time during a dialysis treatment, for example, it may be performed only one time at a commencement of dialysis treatment or may be repeated several times at a constant interval. Accordingly, it is possible to detect the concentration (variation of concentration) of discharged liquid flowing through the dialysate discharging line 8 based on the received light intensity (voltage caused in accordance with the received light intensity of the light receiving means 12) detected by the detecting means 13 if the dialysis treatment is carried out by extracorporeally circulating blood of a patient in the blood circuit 1 and thus it is possible to monitor the blood purification efficiency in real time during a blood purification treatment by operating e.g. an indicator such as "Kt/V" based on the concentration variation.

"Kt/V" is an indicator obtained by substituting the urea nitrogen concentration at times of both commencement and completion of the hemodialysis treatment, a total amount of ultrafiltration during the hemodialysis treatment and a time duration of the ultrafiltration for a predetermined operational expression e.g. such as $Kt/V=-\ln(Ce/Cs)$ (herein "Ce" is the urea nitrogen concentration on time of completion of the hemodialysis treatment and "Cs" is the urea nitrogen concentration on time of commencement of the hemodialysis treatmen). Usually, from this indicator, it is possible to judge that the dialysis efficiency is proper if the value of Kt/V is 1.2 or more. Accordingly, since the variation of urea nitrogen concentration can be known real time from the operational expression above, it is possible to monitor the blood purification efficiency in real time during the blood purification treatment (hemodialysis treatment).

According to the blood purification example, since it includes the correcting device (error corrector) 16 which can not only detect the concentration of discharged liquid based on received light intensity of transmitted light from the light receiving means 12 detected by the detecting means 13 and but also absorb detection error of the discharged liquid concentration sensor (concentration detecting means) 5 based on the received light intensity of reference light from the reference light receiving means 15, it is possible to minimize the detecting error of liquid concentration caused by temperature variation and thus to improve the accuracy of detection of liquid with the discharged liquid concentration sensor (concentration detecting means) 5.

In addition, since the correcting means 16 as an error corrector can correct the current supplied to the light emitting means 11 so that a light amount irradiated by the light emitting means 11 is constant with the passage of time based on the intensity of the reference light received by the reference light receiving means 15, it is possible to automatically carry out the correction for error correction in the discharged liquid concentration sensor (concentration detecting means) 5. Furthermore, since the light emitting means 11 comprises LED (s) and the light receiving means 12 and the reference light receiving means 15 comprise light receiving element(s) being able to generate a voltage corresponding to the received light intensity, it is possible to form the discharged liquid concentration sensor as LED(s) (concentration detecting means) 5 which has the same technical advantages of LED(s) (i.e. long life and light emitting operation at a low temperature for a long term).

In addition, since the concentration detecting means includes the discharged liquid concentration sensor 5 which can monitor the blood purification efficiency by detecting the concentration of discharged liquid from the dialyzer (blood purification instrument) 2, it is possible to improve the accuracy of detection of concentration of discharged liquid during the blood purification treatment and to monitor the blood purification efficiency in real time with high accuracy. Although it is described that the blood purification efficiency (dialysis efficiency) is obtained by calculating the indicator of Kt/V from the concentration of discharged liquid detected by the discharged liquid concentration sensor 5, it is also possible to obtain the blood purification efficiency (dialysis efficiency) by calculating other indicators.

The concentration detecting means is not limited to the discharged liquid concentration sensor 5 and may be formed of a blood leakage detector which is arranged on the dialysate discharging line 8 within the dialysis apparatus 6 and is able to detect leaked blood from a concentration of liquid discharged from the dialyzer (blood purification instrument) 2, or may be formed of a blood concentration detecting sensor (e.g. a hematocrit sensor for measuring the hematocrit value of blood) which is arranged on the blood circuit 1 for extracorporeally circulating blood of a patient and is able to detect the concentration of blood flowing through the blood circuit 1.

If the concentration detecting means is a blood leakage detector which is able to detect leaked blood from a concentration of liquid discharged from the dialyzer (blood purification instrument) 2, it is possible to improve the accuracy of detection of blood leakage in discharged liquid during blood purifying treatment. On the other hand, if the concentration detecting means is a blood concentration detecting sensor which is arranged on the blood circuit 1 for extracorporeally circulating blood of a patient and is able to detect the concentration of blood flowing through the blood circuit 1, it is possible to improve the accuracy of detection of blood concentration during blood purifying treatment.

Figure 5:
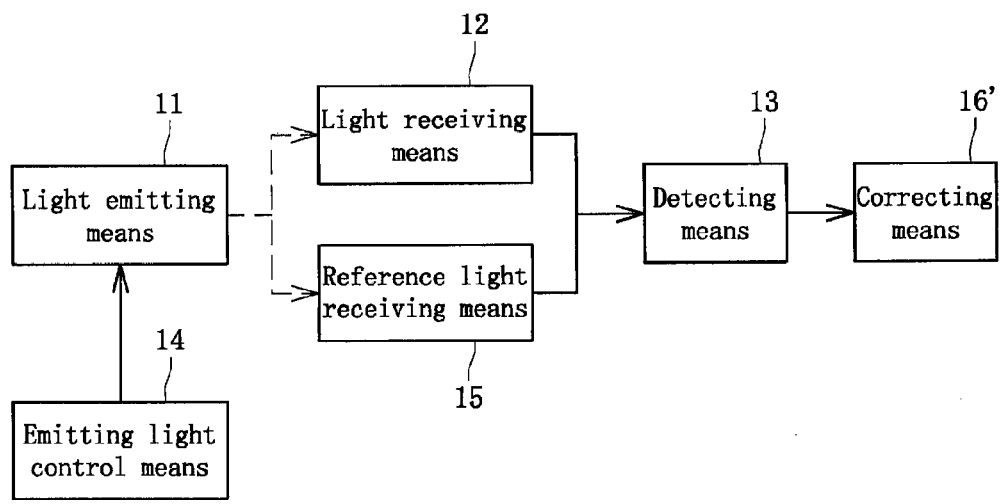
FIG. 5: A block diagram showing a concentration detecting means according to another example of the present invention.

The present invention has been described with reference to the preferred embodiment. Obviously, modifications and alternations will occur to those of ordinary skill in the art upon reading and understanding the preceding detailed description. For example as another example shown in FIG. 5, the error corrector may be formed of a correcting device 16' which can correct a value detected by the detecting means 13 based on the received light intensity of reference light received by the reference light receiving means 15. In particular the correcting device 16' may be structured so that a detected value (received light intensity (received light voltage)) that has been influenced due to the thermal drift can be obtained by obtaining, at first, a rate of change of the received light intensity (received light voltage) of reference light received by the reference light receiving means 15 and, then, by performing a division (back calculation) i.e. by dividing the rate of change by the received light intensity (received light voltage) received by the light receiving means 12.

Similar to the first example, it is also possible in the second example to improve the detection accuracy of concentration of liquid such as discharged liquid or blood detected by the concentration detecting means by minimizing the detection error of concentration due to the temperature variation. In addition, since the error corrector includes the correcting device 16' being able to correct the detected value detected by the detecting means 13 based on the received light intensity of reference light received by the reference light receiving means 15, it is unnecessary to correct the supplying current to the light emitting means 11 and thus to carry out the correction for errors in the concentration detecting means reliably and smoothly as compared with the first example.

Furthermore, in both the first and second example, it is possible to apply the present invention to concentration detecting sensor being able to detect the concentration of liquid in the blood purification apparatus other than the discharged liquid concentration sensor, blood leakage detector or blood concentration sensor etc. In addition, the emitting light control means 14 may be a manually operable one if it comprises the error corrector being able to correct a detected error of the concentration detecting means based on the received light intensity of reference light received by the reference light receiving means 15. That is, it is possible to manually adjust an amount of irradiating light irradiated by the light emitting means 11 in accordance with the correction obtained by the correcting device 16.

Furthermore, although it is described in the example that LED(s) is used as the light emitting means, other appropriate means (e.g. UV lamp, halogen lamp, fluorescent lamp, organic electroluminescent device) may be used as a light source. Although it is described that the present invention is applied to a hemodialysis apparatus, it is possible to apply the present invention to a blood purification apparatus used in other treatments (e.g. blood filtration treatment or blood filtrating dialysis treatment etc.) performing blood purification by an extracorporeal circulation.

The present invention can be applied to a blood purification apparatus having additional functions if the blood purification apparatus is that which can detect concentration of liquid based on a received light intensity of transmitted light detected by a detecting means and has an error corrector being able to correct a detected error of a concentration detecting means based on a received light intensity of reference light received by a reference light receiving means.

What is claimed is:

1. A blood purification apparatus comprising a blood purification instrument comprising a channel for extracorporeally circulating blood of a patient; and
  a concentration detector for detecting a concentration of liquid flowing during blood purification wherein:
  the concentration detector comprises:
  a light emitter for irradiating the channel, through which the liquid is to flow, with light,
  a light receiver for receiving light from the light emitter transmitted through the channel,
  a reference light receiver for receiving reference light which has not been transmitted through the channel;
  a detector for detecting a light intensity respectively of the transmitted light received by the light receiver and a light intensity of the reference light received by the reference light receiver; and
  an error corrector for detecting the concentration of the liquid based on the light intensity of the transmitted light and for correcting a detection error of the concentration detector based on the light intensity of the reference light.

2. The blood purification apparatus of claim 1, wherein the error corrector comprises a correcting device for correcting a current supplied to the light emitter so that a light amount irradiated by the light emitter is constant with passage of time based on the light intensity of the reference light.

3. The blood purification apparatus of claim 1, wherein the error corrector comprises a correcting device for correcting a detected value detected by the detector based on the light intensity of the reference light.

4. The blood purification apparatus of claim 1, wherein the light emitter comprises one or more LEDs and both the light receiver and the reference light receiver comprise a light receiving element for generating a voltage corresponding to received light intensity.

5. The blood purification apparatus of claim 1, wherein the concentration detector is a discharged liquid concentration sensor that monitors a blood purification efficiency by detecting the concentration of the liquid discharged from the blood purification instrument.

6. The blood purification apparatus of claim 1, wherein the concentration detector is a blood leakage detector that detects blood leakage from the concentration of discharged liquid from the blood purification instrument.

7. The blood purification apparatus of claim 1, wherein the concentration detector is arranged on a blood circuit and comprises a blood concentration sensor which detects the concentration of blood flowing through the blood circuit.

8. The blood purification apparatus of claim 1, wherein the reference light is light that branches from the light emitted from the light emitter before entering the channel.

9. The blood purification apparatus of claim 1, wherein the concentration detector is disposed on a dialysate discharging line of a homedialysis apparatus.

* * * * *